(12) United States Patent
Lantz

(10) Patent No.: US 10,761,084 B1
(45) Date of Patent: Sep. 1, 2020

(54) ELECTRONIC CONSENT

(71) Applicant: Herman D. Lantz, Moundsville, WV (US)

(72) Inventor: Herman D. Lantz, Moundsville, WV (US)

(*) Notice: Subject to any disclaimer, the term of this patent is extended or adjusted under 35 U.S.C. 154(b) by 347 days.

(21) Appl. No.: 15/046,049

(22) Filed: Feb. 17, 2016

Related U.S. Application Data

(60) Provisional application No. 62/117,228, filed on Feb. 17, 2015.

(51) Int. Cl.
| | | |
|---|---|---|
| *G01N 33/497* | (2006.01) | |
| *G16H 10/60* | (2018.01) | |
| *H04L 29/06* | (2006.01) | |
| *G16H 15/00* | (2018.01) | |
| *H04W 12/00* | (2009.01) | |
| *G16H 80/00* | (2018.01) | |
| *H04W 12/02* | (2009.01) | |
| *G16H 50/20* | (2018.01) | |
| *G16H 50/30* | (2018.01) | |
| *H04W 12/06* | (2009.01) | |
| *H04W 12/08* | (2009.01) | |
| *G06Q 50/26* | (2012.01) | |
| *G06Q 50/00* | (2012.01) | |
| *A61B 10/00* | (2006.01) | |

(Continued)

(52) U.S. Cl.
CPC ......... *G01N 33/4972* (2013.01); *G06Q 50/01* (2013.01); *G06Q 50/265* (2013.01); *G16H 10/60* (2018.01); *G16H 15/00* (2018.01); *G16H 50/20* (2018.01); *G16H 50/30* (2018.01); *G16H 80/00* (2018.01); *H04L 63/0442* (2013.01); *H04L 63/061* (2013.01); *H04L 63/083* (2013.01); *H04L 63/0823* (2013.01); *H04L 63/0861* (2013.01); *H04L 63/102* (2013.01); *H04W 4/02* (2013.01); *H04W 12/001* (2019.01); *H04W 12/00522* (2019.01); *H04W 12/02* (2013.01); *H04W 12/06* (2013.01); *H04W 12/08* (2013.01); *A61B 2010/0009* (2013.01); *G06Q 50/18* (2013.01)

(58) Field of Classification Search
CPC ...... G01N 33/4972; G06Q 50/18; H04W 4/02
USPC ........................................................ 73/23.3
See application file for complete search history.

(56) References Cited

U.S. PATENT DOCUMENTS

| | | | | |
|---|---|---|---|---|
| 5,418,142 A | * | 5/1995 | Kiser | ............. C12Q 1/54 422/422 |
| 5,458,853 A | * | 10/1995 | Porter | ........... G01N 33/4972 422/84 |

(Continued)

OTHER PUBLICATIONS

Non-Patent Literature "Total DUI", accessed at http://web.archive.org/web/20090218043600/http://www.totaldui.com/breathalyzers/bac/laws-by-state.aspx, archived on Feb. 18, 2009.*

(Continued)

*Primary Examiner* — Daniel S Larkin
*Assistant Examiner* — Anthony W Megna Fuentes

(57) ABSTRACT

Method and apparatus to record consent between two or more sexual partners. If both partners cannot prove certain information, including but not limited to their respective ages and respective levels of intoxication, a consent record will not be generated or a negative consent record will be generated. A "no" or negative record consent cannot be overridden by either of the two partners.

20 Claims, 3 Drawing Sheets

(51) Int. Cl.
*G06Q 50/18* (2012.01)
*H04W 4/02* (2018.01)

(56) References Cited

U.S. PATENT DOCUMENTS

| | | | | |
|---|---|---|---|---|
| 5,580,794 | A * | 12/1996 | Allen | B01L 3/5023 |
| | | | | 422/404 |
| 6,205,840 | B1 * | 3/2001 | Thompson | G01N 33/497 |
| | | | | 422/84 |
| 6,748,792 | B1 * | 6/2004 | Freund | B60K 28/063 |
| | | | | 180/272 |
| 7,400,258 | B2 * | 7/2008 | Crespo | A61B 5/18 |
| | | | | 340/573.1 |
| 7,934,577 | B2 * | 5/2011 | Walter | B60K 28/063 |
| | | | | 180/272 |
| 9,032,486 | B2 * | 5/2015 | Burke | G06Q 50/01 |
| | | | | 705/319 |
| 9,707,845 | B1 * | 7/2017 | Nienhouse | H04Q 9/00 |
| 2009/0157538 | A1 * | 6/2009 | Subramaniam | G06Q 10/10 |
| | | | | 705/35 |
| 2012/0157871 | A1 * | 6/2012 | Walden | A61B 5/097 |
| | | | | 600/532 |
| 2014/0034492 | A1 * | 2/2014 | Fodor | G01N 27/4078 |
| | | | | 204/403.01 |
| 2014/0210627 | A1 * | 7/2014 | Nothacker | G08B 21/02 |
| | | | | 340/576 |
| 2015/0269692 | A1 * | 9/2015 | Ryan | G06Q 50/18 |
| | | | | 705/311 |

OTHER PUBLICATIONS

Highway Safety Title 23, United States Code, Chapter 4 and Related Highway Safety Provisions.*

* cited by examiner

ELECTRONIC CONSENT

CROSS-REFERENCE TO RELATED APPLICATIONS

The present patent application claims the benefit of U.S. Provisional Patent Application Ser. No. 62/117,228, filed Feb. 17, 2015, entitled Electronic Consent, the content of which is hereby incorporated by reference in its entirety.

TECHNICAL FIELD

The various inventive embodiments contained herein generally relate to protecting vulnerable individuals from criminals and preventing unwarranted legal action against innocent individuals.

BACKGROUND

It is sometimes difficult to prove if a sexual act is consensual or non-consensual. Fraud, intoxication, or miscommunication between two potential sex partners can result in rape or sexual assault. On the other hand, fraud or greed can subject one of the sex partners to potential wrongful criminal and civil liability.

CIRCLE of 6 provides a smartphone application (APP) that allows a user to pre-program contact information of six close friends. If a user is put into a potentially threatening situation, the user can use the APP to immediately and automatically notify the six pre-selected friends that the user needs assistance. The APP also provides the location of the user. Although Circle of 6 is an advance in the area of personal safety, the APP does not protect the legal rights of consenting or non-consenting partners.

Another approach is a written consent record between two consenting partners. An example is the Campus Sexual Consent Form, (http://www.bluerepublican.org/wp-content/uploads/2014/09/Campus-Sexual-Consent-Form.pdf). The written consent record is signed prior to the execution of any sexual contact between at least two consenting adults. This approach offers some protection to the partners, but paper consent records can be lost, stolen, laundered in garments, or forged. Moreover, apparent consent can be given by one or more partners even if legal consent is absent. Stated another way, a partner who cannot legally consent due to age, mental maturity, intoxication, etc. can still give apparent but not legal written consent.

Good2Go was an APP used to prove consent. The Good2Go APP relied on self-identification of intoxication and age.

SUMMARY

Embodiments of the present invention may perform several functions, such documenting positive (yes) or negative (no) consent to sexual activity, preventing positive apparent consent where consent cannot legally exist, help insulate innocent partners from wrongful civil or criminal prosecution, help discourage possible extortion of wealthy partners, and help protect vulnerable partners from rape or sexual assault. One aspect of the described embodiments is to create an apparatus and method that pre-empts any ability for a partner to give apparent consent in the absence of legal consent. Although the present invention has some elements that are also found in contracts (mutual agreement), the present invention is not a contract per se because partners can legally withdraw consent at any time without damages or specific performance. There is no legal mechanism to enforce consensual acts. A contract is therefore defined herein as a record of consent, not a legally enforceable offer, acceptance, and validation.

Apparent consent that does not rise to the level of actual or legal consent can be potentially avoided by embodiments of the present invention. For example, one embodiment may include any combination of the following steps: loading personally identifiable information (PII); verifying PII; verifying a level of intoxication; verifying a statutory age of consent; selecting agreed-to consensual acts such as sexual acts; and documenting consent to the agreed-to consensual acts. If an individual cannot satisfy pre-determined criteria such as intoxication, age, etc., a documented consent record (fixed in a tangible medium of expression) cannot be formed or generated between two or more partners.

Another embodiment may include a method to document consensual acts including any of the steps of: proving the age of a partner; proving the intoxication level of the partner; generating a consent record only if the age of the partner meets or exceeds a legal age limit or if the intoxication level is at or below a legal intoxication limit; documenting agreed-to acts; and documenting consent to the agreed-to acts.

Another embodiment may include method to document consensual acts including any of the steps of: proving the identity of a partner and time-stamping the identification; proving the intoxication level of the partner and time-stamping the intoxication level; documenting agreed-to acts and time-stamping the agreed-to acts; and documenting consent to the agreed-to acts and time-stamping the consent.

Another embodiment may include a method to document consensual acts including any of the steps of: using a third party to gather personal identity data; using a third party to verify the veracity of the personal identity data; using a third party to verify the ability to consent to consensual acts; and documenting consent to engage in consensual acts. Third party data verification is helpful because It is unlikely that most individuals can easily access PII from public records within the timeframe of anticipated activities. There is typically a limited time window to gather any necessary information.

Another embodiment may include a method to document consensual acts including any of the steps of: collecting personal identity data using an electronic input or communication apparatus; using the same communication apparatus to collect intoxication information; and using the same apparatus to consent to the consensual acts.

Another embodiment may include a method to document consensual acts including any of the steps of: collecting data that represents the identity of an individual; collecting data that represents an intoxication level of the individual; collecting data that represents the geographical location of the individual; and preventing documented consent if the intoxication level is above a legal intoxication limit for the geographical location.

Another embodiment may include a method to document consent between two partners, including the steps of: verifying identities of the two partners; measuring individual blood alcohol contents of the two partners; and providing a menu of sexual acts to the two partners, but only when the individual blood alcohol contents of the two partners are below a pre-determined intoxication limit. The step of verifying the identities of the two partners may include a step of determining individual ages of the two partners. The step of verifying the identities of the two partners can include a step of accessing a third party database to gather personal identity data. The method can further includes a step of collecting data that represents the current geographical location of the two partners. The identities of the two partners can include respective ages of the two partners, and a further step can include collecting data that represents an age of statutory consent in a current geographical location of the two partners. The step of providing a menu of sexual acts to the two partners only occurs within one hour after the step of measuring individual blood alcohol contents of the two partners.

A method to document consent between two partners can include the steps of: verifying identities of the two partners; verifying intoxication levels of the two partners; and providing a list of sexual acts to the two partners, but only when: (i) the previous steps of verifying the identities of the two partners and verifying intoxication levels of the two partners are completed, and (ii) the intoxication levels of the two partners are below a pre-determined intoxication limit. The step of verifying the intoxication levels of the two partners can be done with a fuel cell sensor. The step of verifying identities of the two partners can include a step of determining individual ages of the two partners. When the list of sexual acts is not presented, this cannot be overridden by either of the two partners. The step of providing the list of sexual acts to the two partners only occurs within one hour after the step of verifying intoxication levels of the two partners.

An apparatus used to document consensual acts between two partners can include a communication apparatus that includes a processor and non-transitory computer readable medium containing program instructions, and a blood alcohol detection device configured to attach to the communication apparatus and transform expelled breath of the two partners into individual blood alcohol contents. The program instructions can cause the processor to perform the steps of verifying identities of the two partners; measuring the individual blood alcohol contents of the two partners as measured by the blood alcohol detection device; and providing the two partners with a menu of sexual acts, but only when the individual blood alcohol contents of the two partners is below a pre-determined limit.

An apparatus used to document consensual acts can include a processor and a non-transitory computer-readable medium having data stored therein representing software executable by the processor. The non-transitory computer-readable medium can include program instructions that verify an identity of a partner, verify an age of the partner, verify a blood alcohol content of the partner, and provide the partner a menu of sexual acts, but only when the blood alcohol content of the partner is below a pre-determined intoxication limit. A blood alcohol detection device can be tied to the apparatus, and transforms expelled breath of the partner into the blood alcohol content of the partner. The identity of the partner can be verified by a time-dated photo of the partner blowing into a blood alcohol detection device. The partner can be provided with the menu of sexual acts within one hour after the blood alcohol content of the partner is verified, but only when the blood alcohol content of the partner is below a pre-determined intoxication. A further step can include creating a complete consent record that contains acts selected from the menu of sexual acts and electronic signatures of the two partners, after the step of providing a menu of sexual acts to the two partners.

Another embodiment may include an apparatus to document consensual acts including any of the following: a communication apparatus and a blood alcohol detection device configured to attach to the communication apparatus and send data such as a blood alcohol content (BAC) to the communication apparatus. The blood alcohol detection device may be configured to transform expelled breath into a BAC that can be recognized by instructions residing on a non-transitory computer readable medium, such as phone, tablet, or computer memory or memory cards. The instructions or software are capable of generating a consent record for consent to acts only if the BAC measured by the blood alcohol detection device is below a specified level such as 0.01, 0.02, 0.08, 0.10 or any other measurable level and preventing consent from being documented if the blood alcohol level is above a specified level, such as 0.00, 0.02, 0.08, 0.10 or any other measurable level.

Another embodiment may include an apparatus that can be used to document consensual acts, the apparatus including any of the following: a communication apparatus; a blood alcohol detection device configured to attach to the communication apparatus and send data to the communication apparatus after a person or party expels exhaled breath into the blood alcohol detection device; and instructions or software that generate a consent record for consent to acts if the BAC measured by the blood alcohol detection device is below a specified BAC level and the person is over a specified age level, such as 16, 17, 18, or 21 depending on the jurisdiction.

Another embodiment may include an apparatus that can be used to document consensual acts, the apparatus including any of the following: a apparatus that can be used to verify the identity and age of a person, verify the blood alcohol content of the person and generate a legal consent record only if the age and blood alcohol content of the person are within pre-determined age and BAC parameters.

Another embodiment includes an apparatus. The apparatus, such as a smartphone, tablet, computer or standalone apparatus may include an electronic apparatus that is in communication with an electronic database. The apparatus may further include a touch screen to input data, a microphone to record voices, a blood alcohol detection device, a camera to record images and video, and software or an APP resident in a non-transitory computer readable medium.

Another embodiment may include a method to document consent, including any of the steps of: verifying and recording the identity of one partner or the identities of two partners; recording an agreed-to act between the two partners; recording or measuring individual blood alcohol contents of the two partners via a blood alcohol detection device; and generating a consent record between the two partners in a tangible medium of expression only if: (i) the previous steps relating to the identities of the partners and blood alcohol contents are successfully completed, (ii) a request for consent record generation occurs within one hour (or any time between and including 1 to 60 minutes) after the step of recording individual blood contents of the two partners and (iii) the individual blood alcohol contents are below a pre-determined intoxication limit, wherein a consent record that documents consent by both of the partners cannot and will not be generated if sub steps (i)-(iii) are not all satisfied. As generally described in the Abstract, if both partners cannot prove certain information, including but not limited to their respective ages and respective levels of intoxication, a negative consent record will be generated. A "no" or negative record consent cannot be overridden by either of the two partners. Further steps may include verifying the identities of the two partners and determining individual ages of the two partners, wherein the step of verifying the identities of the two partners can include the step of accessing a third party database to gather personal identity data. Other steps may include collecting data that represents a current geographical location of two partners and preventing a consent record from being generated if blood alcohol contents of at least one of one of the two partners is above a legal intoxication limit for the geographical location. The identities of the two partners may include the ages of the two partners. Other steps may include collecting data the represents age of consent in a current geographical location of the two partners and preventing a consent record from being generated if either one of the ages of the two partners is below the age of consent in the current geographical location of the two partners. The step of generating a consent record is not possible if either of the two partners has a blood alcohol content 0.08 or higher for partners 21 years of age or older or anything above 0.00 for partners younger than 21 years of age.

Another embodiment may include an apparatus used to document consensual acts between two partners. The apparatus may include any of the following: a communication apparatus capable of running program instructions and a blood alcohol detection device configured to attach to the communication apparatus. The blood alcohol detection device is configured to transform expelled breath of each of the two partners into individual blood alcohol contents and send blood alcohol content data for each of the two partners to the communication apparatus for use by the program instructions. The program instructions may reside in non-transitory computer readable medium. The program instructions, in combination with a processor on the communication apparatus perform the steps of: verifying and recording the identities of the two partners; recording an agreed-to consensual act between the two partners; recording the blood alcohol content data for each of the two partners as measured by the blood alcohol detection device; and generating, after all of the preceding steps have been accomplished and within one hour of the step of recording the blood alcohol content for each of the two partners, a consent record between the two partners. A consent record is not and cannot be generated if any of the individual blood alcohol contents are above a pre-determined limit.

Another embodiment may include an apparatus used to document consensual acts, the apparatus including a processor and non-transitory computer-readable medium having data stored therein representing software executable by the processor, the non-transitory computer-readable medium comprising instructions to verify an identity of a person, verify an age of the person, verify a blood alcohol content of the person, and generate a consent document only if the age of the person is above 18 years of age and the blood alcohol content of the person is below 0.08 and the consent document is requested within one hour after the blood alcohol content of the partner is verified. The consent record is not and cannot be generated if the age of the partner is not 21 years of age or older and the blood alcohol content of the partner is not below 0.08. The apparatus may further include a blood alcohol detection device configured to attach to the communication apparatus and transform expelled breath of the person into a blood alcohol content expressed as a percentage. The non-transitory computer-readable medium may include an instruction to identify a geographical location of the person, an instruction to identify the age of consent law applicable to the geographical location of the person, and an instruction to identify the legal intoxication threshold applicable to the geographical location of the person. The apparatus may be a Smartphone comprising a touch screen to input data, a microphone to record voices, and a camera to record images and video. The microphone may be used to create a voice data file that evidences verbal consent. The camera may be used create a visual data file that evidences visual consent.

Any step or element of any of the embodiments listed above can be combined with any other step or element of the other embodiments listed above or any step or element described below.

BRIEF DESCRIPTION

Figure 1:
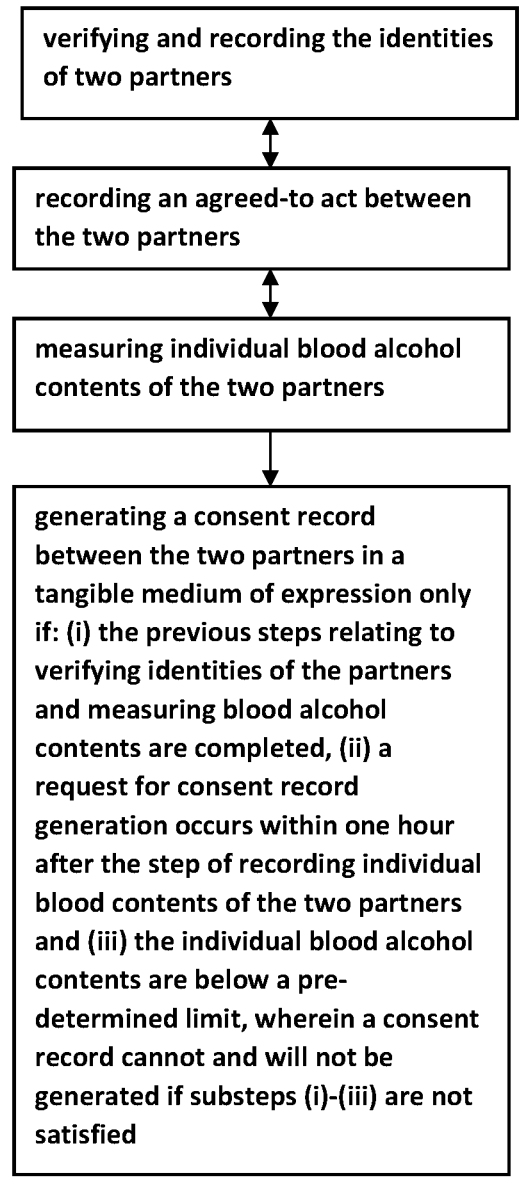
FIG. 1 is a flowchart diagram of a method according to one or more embodiments of the present invention.

One embodiment includes a method to prove consent to sexual activity. The method may include the step of entering, accessing or pre-loading personally identifiable information (PII) of each partner via a smartphone APP, executable instructions, a tablet APP, database, computerized software program or database, the Internet, Wi-Fi, a database stored in a standalone apparatus, or other electronic databases such as a third party database. PII may include but is not limited to a driver's license number, phone number, mailing address, pre-assigned personal identification number (PIN), finger lock/unlock patterns, military identification, government issued ID card, Social Security Account Number, fingerprint, voice sample, facial recognition, signature, or photograph. PII may be entered into an apparatus or database by touch screen, audio recording, magnetic point-of-sale (POS) cards and readers, memory cards and readers, SIM cards and readers, biometric (fingerprint, retina, facial) readers, RFID cards and readers, smart cards and readers, QR codes and scanners, UPC codes and scanners, etc. Any of these forms of identification can be used independently or in any combination.

Another step may include verifying and possibly recording the identities, ages, known criminal records, known infectious disease status, etc. of the partners based on the entered PII. A driver's license can be falsified or swiped by someone other than the owner of the license, so two or more forms of independent identification may be needed and cross-checked by an APP, instructions, service provider or other third party database service provider. Redundant methods of age verification, such as cross-checking information with known public or governmental databases, is contemplated to help discourage fraud. Therefore, another step may be corroborating PII with a publicly available or proprietary third party database, a more restricted governmental database, a law enforcement database, etc.

PII can be pre-stored in a secure database and accessed at any time by internet or cell phone connectivity. As a non-limiting example, a person who is already verified (identity and age) can log onto the APP using an affirmative act, such as entering a secret PIN or other logon credentials only known to the person accessing the APP, software, instructions, or database. For added security all of the partners, a secondary form of identification can be prompted by the APP or instructions. Examples may include a Social Security account number or swiping a driver's license card or other physical identification card using a phone point of sale (POS) reader, such as Square Reader (http://www.squareup.com), or other card reader or scanner. The login sequence can be done in a variety of ways. It is contemplated that all of the partners can login using a common apparatus, such as a single smartphone. The APP, instructions, or software can prompt all partners to enter a PIN or other secure login credentials known only to the respective partners. The APP or instructions may then prompt for more partners or ask if all partners have been entered. Alternatively, login can be done by separate smartphone, computers, tablets or other apparatuses.

Once each partner has entered their respective access credentials, and the credentials are verified, the APP/instructions/software can automatically generate a pre-consent record populated with personal identifying information or, for privacy, a more anonymous coded username or user ID associated with the true identity of the partner. If a potential partner is not registered or is not found in a secure database of APP or software users, the non-registered partner can register at that time via a registered user's apparatus or register by a separate apparatus. On-the-spot registration is contemplated, such as by uploading a photo of the person along with some verification of identity and age. However, since this method risks the disclosure of address, driver's license number and other personally identifying information to another partner, another option is that each partner can pre-register prior to any contemplated sexual activity. Registration can be free or be fee based.

When the PII contained in the secure database is accessed, modified, supplemented, or deleted by a person who accessed the database via a manual access method or manual access plus backup credentials, a time stamp may be generated and recorded. All time stamps may be generated by a clock in the APP instructions, a processor, firmware, or other accurate time generation apparatus and can be automatically adjusted by time zone according the to the geographic location of the smartphone, computer IP address, or IP service provider. The time stamps create a timeline that can be used by law enforcement, prosecutors, or defense attorneys to re-create a chronological series of events.

An additional step may include taking a blood alcohol reading by a blood alcohol detection device, such as by a BACTRACK Mobile Breathalyzer (BLUETOOTH connection to smartphone), an AlcoMate AccuCell AL9000 Fuel Cell Breathalyzer with computer-ready USB port, the IPEGA Backlight Alcohol Breath Tester for Samsung Smartphone with Micro USB port, a Sharper Image APPLE iPHONE Breathalyzer with APPLE iPHONE connector, or other suitable apparatus. The blood alcohol detection device transforms exhaled air, vapor, or other collected bodily fluid into a blood alcohol content reading, such as by a fuel cell sensor. The blood alcohol content reading of the partners can also be done before or after identity and age are confirmed, and can be used to stop the consent process. Another consideration is that it is common for college-aged adults to consume alcohol or other intoxicating substances even though they are under the legal drinking age or the substances are otherwise banned by local, state, or federal law. The purpose of the BAC level test is not to prove a violation of local liquor laws, but rather act as gate that prevents further steps of documented consent from being performed. For this reason, it is contemplated that recordation of BAC levels can be recorded in all instances or only if alcohol levels of the partners fall below 0.02, 0.08, 0.10 or some other level. In instances where BAC levels of any partner is above a pre-defined threshold based on local law, perhaps as low as 0.00 or 0.02 for adults under legal drinking age or 0.08 or 0.10 for adults over legal drinking age, the partner is prevented from verifying consent to any sexual acts.

Naturally, partners can still engage in sexual acts even if the embodiments described herein are ignored or bypassed. However, this defeats the legal protection that the disclosed embodiments attempt to preserve. It is also contemplated that partners can upload a time-dated photo of the individual partners blowing into the blood alcohol detection device or a time dated photo is automatically taken as a partner is blowing into the blood alcohol detection device or at some finite time thereafter. The concern is that someone other than the partner can blow into the blood alcohol detection device. A secondary confirmation step of some kind (PIN, photo, video, voice, etc.) may be necessary to prevent fraud. It may also be important to put a time limit such as 1-60 minutes between BAC detection and consent since BACs can rise as more alcohol is consumed.

Once the intoxication level of the partners is verified or recorded or before intoxication is measured, another step may include providing the partners with a menu of mutually acceptable sexual acts. Since this patent application is a public document, sexual acts are not listed in graphic detail. However, any type of consensual sexual contact that can occur between consenting adults is contemplated, regardless of moral or legal prohibition. A list of acts that are not to be attempted can also be presented and agreed to. As another available step, the partners can enter the location of the sexual activity or have the location determined by Global Positioning (GP) and receive a summary of sexual acts that may be banned by law in that jurisdiction and consent ages in that jurisdiction. Alternatively, only acts permitted in that jurisdiction may display in a menu available to the partners. This step of limiting activity bases on jurisdictional law may further contain a mutual stipulation that neither partner is free to disclose to law enforcement any agreed-to acts that may violate local decency or statutory laws solely for the purpose of proving that the partners violated a local law.

It is contemplated that a time limit for consent, separate from the time limit between alcohol testing and documented consent, can also be agreed to by the partners. Consent can be given for a definite time period such as an hour, a day, etc. The consent record terms can also include a confidentiality statement, a confirmation that the partners are not married, a confirmation that neither partner has a communicable disease, a confirmation that birth control or barrier protection will be used by a designated partner, an agreed-to safe word, etc.

After the partners agree to consensual sexual acts and other criteria are met, both partners can digitally approve the agreed-to terms via electronic signature, PIN, Social Security Account Number, driver's license number, or other suitable acknowledgement and proceed to engage in the agreed-to sexual acts. The terms may be agreed to by using a different PII than one used above to determine identity. There may also be a warning that consent of a partner may be terminated is a safe word, "no" or "stop" is uttered or otherwise expressed by the partner. The complete consent record may be retained indefinitely or otherwise beyond an applicable statute of limitations in a secure database and can be automatically assigned a reference number or name for retrieval at a later date. All consent records can be provided and retained free of charge, included in the initial APP or software download fee, or billed separately or jointly per consent record depending on the agreement of the partners. Each partner to the consent record may have the ability to receive an e-copy of the consent record delivered to email or phone or print from the APP or associated website.

Figure 2:
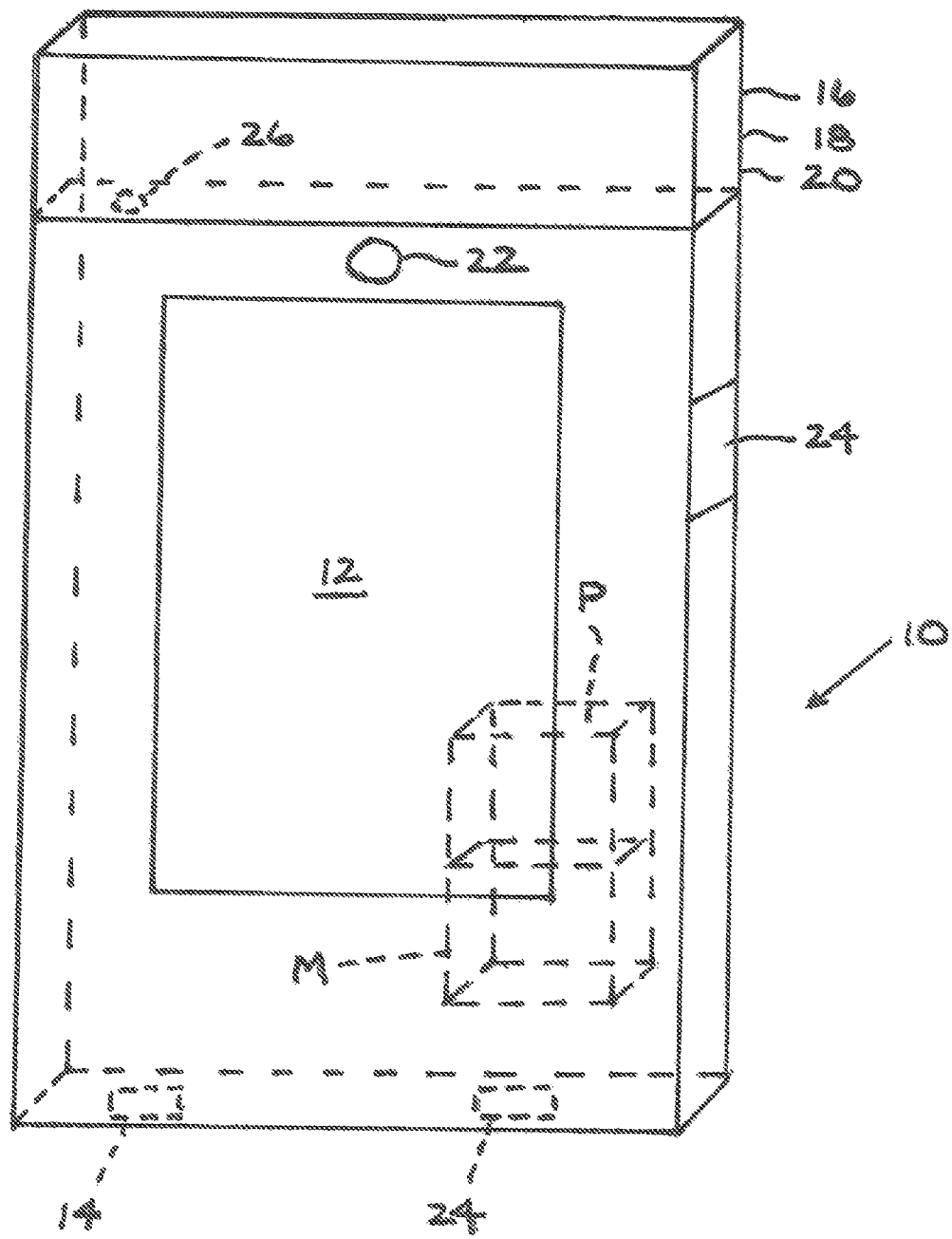
FIG. 2 is a schematic diagram of an apparatus according to one or more embodiments of the present invention.
Figure 3:
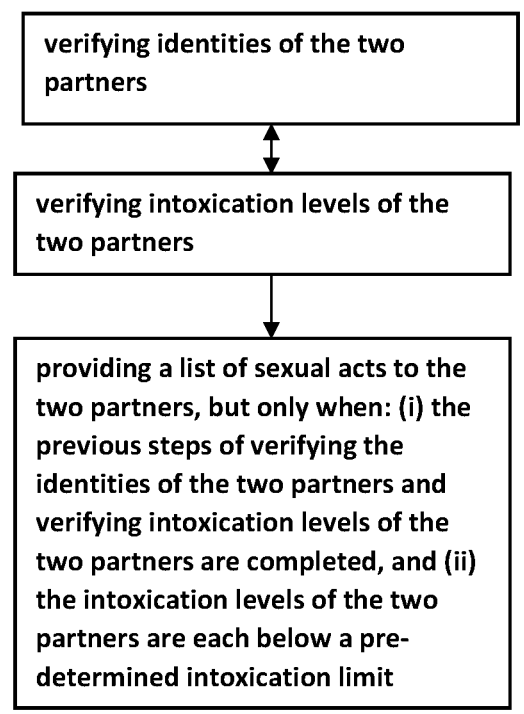
FIG. 3 is a flowchart diagram of a method according to one or more embodiments of the present invention.

Referring to FIG. 2, another embodiment includes an apparatus such as a communication apparatus 10. The apparatus 10, such as a Smartphone (iPHONE, ANDROID, etc.), tablet (APPLE iPAD, NEXUS, etc.), or standalone electronic apparatus may include a processor P, memory or non-transitory computer readable medium M, I/O connections, and an APP, instructions, or software resident in the non-transitory computer readable medium that is capable of performing all or some of the method steps listed above, in any order. The apparatus 10 may further include a touch screen 12 to input data or signatures, a microphone 14 to record voices, a blood alcohol detection device 16, a magnetic card reader 18, and a flash or memory card reader 20 that can all be removeably attached to an I/O port 26, a camera 22 to record images and video, in-out (I/O) data capability 24 to include Wi-Fi, cellular connectivity, and hardwire connections capable of data transmission to a computer or printer. The apparatus 10 and the blood alcohol detection device 16 can be tied directly with the APP, instructions, or software such that the instructions will not generate a signature-ready consent record or consent record unless certain criteria have been measured and verified. For example, one embodiment can ensure that no consent record is generated by the APP/instructions/software unless age and sobriety values are within pre-defined limits. The pre-defined limits can include the legal limits in a particular geographic location. The blood alcohol detection device transforms exhaled breath into digital or analog data that can be used by the APP/instructions/software.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts and steps described above with the above-described embodiments may be employed alone or in combination with any of the other concepts, steps and embodiments described above. It should be further appreciated that the various alternative embodiments described above with respect to one illustrated embodiment can apply to all embodiments as described herein, unless otherwise indicated. Any method step, action, data input, or apparatus element described herein can be used alone or in combination with any other method step, action, data input, or apparatus element described herein.

I claim:

1. A method to document consent between two partners comprising the steps of:
   verifying identities of the two partners;
   measuring individual blood alcohol contents of the two partners; and
   providing a menu of sexual acts to the two partners, but only when the individual blood alcohol contents of the two partners are below a pre-determined intoxication limit.

2. The method as claimed in claim 1, wherein the step of verifying identities of the two partners includes a step of determining individual ages of the two partners.

3. The method of claim 1, wherein the step of verifying identities of the two partners includes a step of accessing a third party database to gather personal identity data of each of the two partners.

4. The method as claimed in claim 1, further comprising a step of collecting data that represents the current geographical location of the two partners.

5. The method as claimed in claim 1, wherein the identities of the two partners include respective ages of each of the two partners and further comprising a step of collecting data that represents an age of statutory consent in a current geographical location of the two partners.

6. The method as claimed in claim 1, wherein the step of providing a menu of sexual acts to the two partners only occurs within one hour after the step of measuring individual blood alcohol contents of the two partners.

7. The method as claimed in claim 1, further comprising a step of creating a complete consent record that contains sexual acts selected from the menu of sexual acts and electronic signatures of the two partners, after the step of providing the menu of sexual acts to the two partners.

8. An apparatus used to document consensual acts between two partners comprising: a communication apparatus comprising a processor and non-transitory computer readable medium containing program instructions; a blood alcohol detection device configured to attach to the communication apparatus and transform expelled breath of the two partners into individual blood alcohol contents; wherein the program instructions cause the processor to perform the steps of: verifying identities of the two partners; measuring the individual blood alcohol contents of each of the two partners as measured by the blood alcohol detection device; and providing the two partners with a menu of sexual acts, but only when the individual blood alcohol contents for each of the two partners is below a pre-determined intoxication limit.

9. An apparatus used to document consensual acts comprising:
   a processor;
   a non-transitory computer-readable medium having data stored therein representing software executable by the processor, the non-transitory computer-readable medium comprising program instructions that verify an identity of a partner, verify an age of the partner, verify a blood alcohol content of the partner, and provide the partner a menu of sexual acts, but only when the blood alcohol content of the partner is below a pre-determined intoxication limit.

10. The apparatus of claim 9, further comprising a blood alcohol detection device that is tied to the apparatus and transforms expelled breath of the partner into the blood alcohol content of the partner.

11. The apparatus of claim 10, wherein the identity of the partner is verified by a time-dated photo of the partner blowing into the blood alcohol detection device.

12. The method as claimed in claim 9, wherein the partner is provided with the menu of sexual acts within one hour after the blood alcohol content of the partner is verified, but only when the blood alcohol content of the partner is below the pre-determined intoxication limit.

13. A method to document consent between two partners comprising the steps of:
   verifying identities of the two partners;
   verifying intoxication levels of the two partners; and
   providing a list of sexual acts to the two partners, but only when: (i) the previous steps of verifying the identities of the two partners and verifying intoxication levels of the two partners are completed, and (ii) the intoxication levels of the two partners are each below a pre-determined intoxication limit.

14. The method as claimed in claim 13, wherein the step of verifying the intoxication levels of the two partners is done with a fuel cell sensor.

15. The method as claimed in claim 13, wherein the step of verifying identities of the two partners includes a step of determining individual ages of the two partners.

16. The method as claimed in claim 13, wherein when the list of sexual acts is not presented, this cannot be overridden by either of the two partners.

17. The method as claimed in claim 13, wherein the step of providing the list of sexual acts to the two partners only occurs within one hour after the step of verifying intoxication levels of the two partners.

18. The method as claimed in claim 13, wherein the step of verifying identities of the two partners includes a step of accessing a third party database to gather personal identity data of each of the two partners.

19. The method as claimed in claim 13, further comprising a step of collecting data that represents the current geographical location of the two partners.

20. The method as claimed in claim 13, wherein the identities of the two partners includes respective ages of the two partners and further comprising a step of collecting data that represents an age of statutory consent in a current geographical location of the two partners.

\* \* \* \* \*